United States Patent
Hall

(10) Patent No.: US 8,668,943 B2
(45) Date of Patent: Mar. 11, 2014

(54) HAIR CARE COMPOSITIONS FOR PROMOTING HAIR GROWTH AND PREVENTING HAIR LOSS

(76) Inventor: Gwendolyn L. Hall, Little Rock, AR (US)

( * ) Notice: Subject to any disclaimer, the term of this patent is extended or adjusted under 35 U.S.C. 154(b) by 0 days.

(21) Appl. No.: 13/443,817

(22) Filed: Apr. 10, 2012

(65) Prior Publication Data

US 2013/0266674 A1    Oct. 10, 2013

(51) Int. Cl.
| | | |
|---|---|---|
| *A61K 36/534* | (2006.01) | |
| *A61K 36/23* | (2006.01) | |
| *A61K 36/53* | (2006.01) | |
| *A61K 8/97* | (2006.01) | |

(52) U.S. Cl.
CPC .............. *A61K 36/534* (2013.01); *A61K 36/23* (2013.01); *A61K 36/53* (2013.01); *A61K 8/97* (2013.01)
USPC .......................................... 424/747

(58) Field of Classification Search
CPC .................................... A61K 36/534
See application file for complete search history.

(56) References Cited

U.S. PATENT DOCUMENTS 7,887,857 B1 *   2/2011   Johnson ................. 424/725
2010/0092582 A1 *   4/2010   Anderson ............... 424/727

OTHER PUBLICATIONS

Abderhalden, H. "About Shea Butter". Dec. 2004. Web Archive Date: Feb. 14, 2005 [Retrieved from the Internet on: Jul. 30, 2013]. Retrieved from: <URL: http://web.archive.org/web/20050214003316/http://www.ghana-help.ch/Shea%20Butter.htm>.*

* cited by examiner

*Primary Examiner* — Amy L Clark
(74) *Attorney, Agent, or Firm* — Richard Blakely Glasgow

(57) ABSTRACT

A hair care composition that prevents hair loss and stimulates hair growth is disclosed. The hair care composition of the present invention comprises natural ingredients including one and/or more carrier oils, one and/or more essential oils, and fragrance oil. The preferred embodiment including Shea Butter, Extra Virgin Olive oil, Jojoba oil, Vanilla fragrance oil, Peppermint essential oil, Lavender essential oil, Tea Tree essential oil, Clary Sage essential oil, and Rosemary essential oil is provided.

2 Claims, No Drawings

HAIR CARE COMPOSITIONS FOR PROMOTING HAIR GROWTH AND PREVENTING HAIR LOSS

BACKGROUND OF THE INVENTION

1. Field of the Invention

The present invention relates to hair care compositions, and more particularly to hair care compositions that contain a novel blend of natural ingredients which can be applied to the scalp and/or hair of a user to prevent hair loss and stimulate hair growth.

2. Description of Related Art

Hair loss, also known as alopecia, may be caused naturally by the effect of hormone (androgens) on the base of the hair bulb, deficiency in nutrition of the hair due to decrease in the micro-circulation in the scalp, or aging of the follicle cells due to lack of care. Hair loss can be caused by a number of medical conditions including thyroid disorders and autoimmune diseases. Hair loss can also be caused by the use of certain therapeutic drugs designed to alleviate conditions such as cancer. Hair loss is a common problem encountered by patients who receive chemotherapy or drugs used to inhibit the immune response, etc. Patients start to develop bald spots in certain places because the hair would fall out again after it grows to a certain point. Patients may have scabs, severe dryness, and bumps on their scalps. The hair is fragile, easy to break off and fall out. Often, such hair loss is accompanied by lack of hair re-growth, leading to partial or full baldness. For aesthetic purpose, most patients need to wear wigs and get extension braids in their hair, which are uncomfortable and inconvenient.

Various agents have been commercialized for improving hair re-growth or growth. Commercially available hair re-growth or growth agents include synthetic chemicals such as vasodilators, hormone drugs for inhibiting action of male sex hormone, etc. However, these synthetic chemicals have undesirable effects on most people. People who have medical conditions or are receiving medical therapy such as chemotherapy, radiotherapy, or drugs used to inhibit the immune response, etc. should avoid using harsh chemicals on their hair and scalp as these can cause the scalp to become dry and itchy.

The use of herbal products including essential oils or carrier oils provides benefits over and above the aforementioned synthetic chemicals, etc. Essential Oils contained in plants have a very beneficial effect on hair growth. Studies suggest that one or more of the essential oils are biologically able to promote hair growth. Essential oils for hair growth are excellent for cleansing, nourishing, and strengthening the hair follicle and shaft. These essential oils for hair growth stimulate the hair follicles to grow faster than the hair would normally. However, most essential oils are highly concentrated and potent, they may have adverse effect on skin if used undiluted. It is ideal to dilute essential oils with carrier oils. Carrier oils are a vegetable origin extracted from nuts and seeds by cold pressing. Carrier oils provide lubrication and moisture and help with the absorption of essential oils into the skin. Moreover, carrier oils alone also provide nutrition and moisture to dry or damaged hair.

Some products and compositions that contain herbal products have been disclosed for enhancing hair growth. More specifically, by way of example, U.S. PreGrant Pub. No. 20090123564 to Jain et al. discloses a novel composition for hair loss and/or hair growth promotion comprising active agent derived from natural source such as from the plant *Vernonia* sp., either alone or in combination with other active agents that are obtained from a natural source selected from a group comprising Aloe, Burdock, Capsicum, Ginger, Ginkgo, Green Tea, Hip, Lavender, Milfoil, Nettles, Onion, Pygeum, Rattanjot, Red Pepper, Rosemary, Safflower oil, and Tea Tree oil, or mixture thereof.

The hair care compositions disclosed in the present application are distinguished from the invention disclosed in U.S. PreGrant Pub. No. 20090123564, because the present invention comprises certain essential oils or carrier oils, which are not contained in the composition disclosed in U.S. PreGrant Pub. No. 20090123564.

By way of example, U.S. Pat. No. 7,887,857 B1 to Johnson (2011) discloses a shampoo consisting of a clear shampoo base (65%), Pomace Olive oil (7.5%), Coconut oil (7.5%), Corn starch-based rheology modifier and emulsion stabilizer (7.5%), Jojoba oil (3.8%), Avocado oil (3.8%), functional Honey (3.8%), Tea Tree oil (0.08%), Hemp seed oil (0.08%), Shea oil (0.08%), Peppermint oil (0.08%), Rosemary Oleoresin extract (0.05%), Lemongrass oil (0.05%), Ylang-ylang oil (0.05%), and Clary Sage oil (0.05%).

The hair care compositions disclosed in the present application are distinguished from the invention disclosed in U.S. Pat. No. 7,887,857 B1 to Johnson in that the present invention comprises Lavender essential oil, which is not contained in the composition disclosed in U.S. Pat. No. 7,887,857 B1. Lavender essential oil is significant towards people who receive medical therapy that leads to severe dryness, bumps, and scabs because it can increase the rate of wound healing. Moreover, the percentage of each ingredients of the present invention is significantly different from the range disclosed in U.S. Pat. No. 7,887,857 B1.

Therefore, although numerous compositions and methods for stimulation of hair growth are known in the art, there is still a need to provide different compositions that are suitable for people who have hair loss due to medical conditions or drug therapy.

SUMMARY OF THE INVENTION

In an exemplary embodiment of the present invention, there is disclosed a hair care composition being formulated for topical application on users' scalp. The composition comprises one and/or more carrier oil, one and/or more essential oil, and one and/or more fragrance oil. The carrier oils may be selected from a group consisting of Extra Virgin Olive oil, Jojoba oil, Shea Butter, and any combinations thereof. The essential oils may be selected from a group consisting of Clary Sage essential oil, Rosemary essential oil, Peppermint essential oil, Lavender essential oil, Tea Tree essential oil, and any combinations thereof. The fragrance oil may be selected from a group consisting of Vanilla fragrance oil, Lemon fragrance oil, Orange fragrance oil, and any combination thereof.

The hair care compositions of the present invention has demonstrated that they can strengthen hair, prevent hair loss and promote hair growth. The hair care compositions also help to relieve users from medical therapy caused severe dryness, bumps, and scabs in the scalp.

The hair care composition according to the preferred embodiment of the present invention comprises Extra Virgin Olive oil (about 28.6% by volume), Jojoba oil (about 19.0% by volume), Shea Butter (about 38.1% by volume), Peppermint essential oil (about 2.4% by volume), Rosemary essential oil (about 1.2% by volume), Tea Tree essential oil (about 2.4% by volume), Clary Sage essential oil (about 1.2% by volume), Lavender essential oil (about 2.4% by volume), and Vanilla fragrance oil (about 4.8% by volume).

It is to be understood that the aforementioned components and percentage are only exemplary and that various arrangements are possible in other embodiments. The Extra Virgin Olive oil may be present in an amount of 23-34% by volume; the Shea Butter may be present in an amount of 30-46% by volume; the Jojoba oil may be present in an amount of 15 to 23% by volume; the Peppermint essential oil may be present in an amount of 1.2 to 3.6% by volume; the Rosemary essential oil may be present in an amount of 0.6 to 1.8% by volume; the Tea Tree essential oil may be present in an amount of 1.2 to 3.6% by volume; the Clary Sage essential oil may be present in an amount of 0.6 to 1.8% by volume; the Lavender essential oil may be present in an amount of 1.2 to 3.6% by volume; the Vanilla fragrance oil may be present in an amount of 2.4 to 7.2% by volume.

The more important features of the invention have thus been outlined in order that the more detailed description that follows may be better understood and in order that the present contribution to the art may better be appreciated. Additional features of the invention will be described hereinafter and will form the subject matter of the claims that follow.

Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in various ways. Also it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The foregoing has outlined, rather broadly, the preferred feature of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention and that such other structures do not depart from the spirit and scope of the invention in its broadest form.

DESCRIPTION OF THE PREFERRED EMBODIMENT

In an exemplary embodiment of the present invention, there is disclosed a hair care product composition being formulated for topical application on users' scalp. The composition comprises one and/or more carrier oil, one and/or more essential oil, and one and/or more fragrance oil. The carrier oils may be selected from a group consisting of Extra Virgin Olive oil, Jojoba oil, Shea Butter, and any combinations thereof. The essential oils may be selected from a group consisting of Clary Sage essential oil, Rosemary essential oil, Peppermint essential oil, Lavender essential oil, Tea Tree essential oil, and any combinations thereof. The fragrance oil may be selected from a group consisting of Vanilla fragrance oil, Lemon fragrance oil, Orange fragrance oil, and any combinations thereof.

Olive oil, Jojoba oil, and Shea butter work as lubricant and moisturizer, as well as carrier oil for essential oils and aids in the delivery of their healing properties without irritation. They are beneficial to the dry and damaged hair and/or skin and promote hair growth.

Application of Olive oil along with some essential oils is found to be one of the most effective treatments to cure the problem of dry or damaged hair and also for promoting hair growth. The hair is nourished and will regain its elasticity after a treatment with this oil. The molecular structure of Jojoba oil is similar to sebum, which is naturally occurring oil in human hair. This makes it a great choice for a moisturizer. It is one of the best essential oils to stop hair loss due to hair breakage. Shea butter is highly moisturizing, semi-soft substance used as a carrier of essential oils especially where there is damaged, dry or aging skin.

Peppermint helps to stimulate blood flow to the root of hair and so give hair good nutrition and helps it grow well.

Rosemary essential oil is known to promote increased circulation as well as help remove dandruff and sebum accumulations on the scalp.

Tea Tree essential oil works great for unblocking the hair follicles. Blocked hair follicles, caused by oil, dirt or dry skin cells, lead to a number of problems, including thinning and even loss of the hair itself. Thus, application of Tea Tree essential oil leads to hair growth, nourishment of hair and also cleans the dandruff. Furthermore, Tea Tree essential oil is known for its anti-fungal, anti-bacterial, antiseptic properties.

Clary Sage essential oil helps reduce excess hair oil and stimulates dormant hair follicles so they return to the anagen (growing) stage in the hair growth cycle. In addition, this oil kills bacteria and protects against new infections.

Lavender essential oil has been shown to promote the growth of hair and increase the rate of wound healing. Lavender essential oil has very strong anti-inflammatory properties to help combat Alopecia. It may play critical role in helping users' relief from medical therapy caused severe dryness, bumps, and scabs in the scalp.

Referring to Table 1, there is disclosed a hair care composition with a number of different components in varying quantities in order to achieve a desired result. By way of example, the hair care composition may be provided as a topical application on scalp of a user. One such exemplary embodiment of the hair care composition is provided as shown in Table 1.

TABLE 1

| Component | Percentage by volume (% v/v) |
| --- | --- |
| Shea butter | 30-46 |
| Extra Virgin Olive oil | 23-34 |
| Jojoba oil | 15-23 |
| Vanilla Fragrance Oil | 2.4-7.2 |
| Peppermint Essential Oil | 1.2-3.6 |
| Lavender Essential Oil | 1.2-3.6 |
| Tea Tree Essential Oil | 1.2-3.6 |
| Clary Sage Essential Oil | 0.6-1.8 |
| Rosemary Essential Oil | 0.6-1.8 |

Referring to Table 2, there is disclosed a preferred embodiment of the hair care composition according to the present invention.

TABLE 2

| Component | Percentage by volume (% v/v) |
|---|---|
| Shea butter | 38.1% |
| Extra Virgin Olive oil | 28.6% |
| Jojoba oil | 19.0% |
| Vanilla Fragrance Oil | 4.8% |
| Peppermint Essential Oil | 2.4% |
| Lavender Essential Oil | 2.4% |
| Tea Tree Essential Oil | 2.4% |
| Clary Sage Essential Oil | 1.2% |
| Rosemary Essential Oil | 1.2% |

In one embodiment, the hair care composition of the present invention is prepared by measuring about 8 ounces of solid Shea butter into a pan, melting it to a liquid, adding about 4 ounces of the Jojoba and 6 ounces of the Extra Virgin Olive oils to the melted Shea butter. Mixing these carrier oils by hand mixer. Adding about 0.25 ounce of Clary Sage and about 0.25 ounce of Rosemary essential oils into the mixture and mixing again. Then, adding about 0.5 ounces of Peppermint and about 0.5 ounces of Lavender oils into the mixture and mixing again. Adding about 0.5 ounces Tea Tree essential oil into the mixture and mixing again. Finally, adding about 1 ounce of Vanilla fragrance oil to the mixture and mixing. The resulting hair care composition is kept in a freezer for about 7-10 minutes. Removing the product from freezer and mixing again, and then refreezing the product for about five more minutes. Repeat the last steps for three more times. The final product is stored in freezer for at least four days before use.

It is to be understood that the aforementioned components and volumes as well as steps are only exemplary and that various arrangements are possible in other embodiments.

While there have been shown and described and pointed out the fundamental novel features of the invention as applied to the preferred embodiments, it will be understood that the foregoing is considered as illustrative only of the principles of the invention and not intended to be exhaustive or to limit the invention to the precise forms disclosed. Obvious modifications or variations are possible in light of the above teachings. The embodiments discussed were chosen and described to provide the best illustration of the principles of the invention and its practical application to enable one of ordinary skill in the art to utilize the invention in various embodiments and with various modifications as are suited to the particular use contemplated All such modifications and variations are within the scope of the invention as determined by the appended claims when interpreted in accordance with the breadth to which they are entitled.

What is claimed is:

1. A hair care composition for treating hair loss, strengthening hair and for treating scalp dryness, bumps and scabs, said composition consisting essentially of:
   (a) an effective amount of extra virgin olive oil, wherein said effective amount of said extra virgin olive oil is 23-34% by volume;
   (b) an effective amount of shea butter, wherein said effective amount of said shea butter is 30-46% by volume;
   (c) an effective amount of jojoba oil, wherein said effective amount of said jojoba oil is 15-23% by volume;
   (d) an effective amount of peppermint essential oil, wherein said effective amount of said peppermint essential oil is 1.2-3.6% by volume;
   (e) an effective amount of rosemary essential oil, wherein said effective amount of said rosemary essential oil is 0.6-1.8% by volume;
   (f) an effective amount of tee tree essential oil, wherein said effective amount of said tee tree essential oil is 1.2-3.6% by volume;
   (g) an effective amount of clay sage essential oil, wherein said effective amount of said clay sage essential oil is 0.6-1.8% by volume;
   (h) an effective amount of lavender essential oil, wherein said effective amount of said lavender essential oil is 1.2-3.6% by volume; and
   (i) an effective amount of vanilla fragrance oil, wherein said effective amount of said fragrance oil is 2.4-7.2% by volume.

2. The hair care composition of claim 1, wherein said effective amount of said extra virgin olive oil is about 28.6% by volume, wherein said effective amount of said shea butter is about 38.1% by volume, wherein said effective amount of said jojoba oil is about 19% by volume, wherein said effective amount of said peppermint essential oil is about 2.4% by volume, wherein said effective amount of said rosemary essential oil is about 1.2% by volume, wherein said effective amount of said tea tree essential oil is about 2.4% by volume, wherein said effective amount of said clay sage essential oil is about 1.2% by volume, wherein said effective amount of said lavender essential oil is about 2.4% by volume, wherein said effective amount of said vanilla fragrance oil is about 4.8% by volume.

* * * * *